United States Patent [19]

Jones et al.

[11] Patent Number: 5,830,178
[45] Date of Patent: Nov. 3, 1998

[54] METHODS FOR EMBOLIZING VASCULAR SITES WITH AN EMBOILIZING COMPOSITION COMPRISING DIMETHYLSULFOXIDE

[75] Inventors: Michael L. Jones, Capistrano Beach, Calif.; Richard J. Greff, St. Pete Beach, Fla.

[73] Assignee: Micro Therapeutics, Inc., San Clemente, Calif.

[21] Appl. No.: 730,701

[22] Filed: Oct. 11, 1996

[51] Int. Cl.⁶ .................................................. A61M 31/00
[52] U.S. Cl. ............................................................ 604/49
[58] Field of Search ........................... 604/49, 30, 65–67, 604/118, 246

[56] References Cited

FOREIGN PATENT DOCUMENTS

WO97/04657  2/1997  WIPO .

OTHER PUBLICATIONS

Derwent Abstract No. XP 002037148.
Mandai, et al., "Direct Thrombosis of Aneurysms with Cellulose Acetate Polymer", *J. Neurosurg.*, 77:497–500 (1992).
Kinugasa, et al., "Direct Thrombosis of Aneurysms with Cellulose Acetate Polymer", *J. Neurosurg.*, 77:501–507 (1992).
Casarett and Doull's *Toxicology,* Amdur et al., Editors, Pergamon Press, New York, pp. 661–664 (1975).
Kinugasa, et al., "Early treatment of Subarachnoid Hemorrhage After Preventing Rerupture of an Aneurysm", *J. Neurosurg.*, 83:34–41 (1995).
Kinugasa, et al., "Prophylactic Thrombosis to Prevent New Bleeding and to Delay Aneurysm Surgery", *Neurosurg.*, 36(4):661–667 (1995).
Taki, et al., "Selection and Combination of Various Endovascular Techniques in the Treatment of Giant Aneurysms", *J. Neurosurg.*, 77:37–42 (1992).
Sampei, et al., *Interventional Neuradiology,* for "Histological Changes in Brain Tissue and Vasculature after Intracarotid infusion of Organic Solvents in Rats", 38:291–294 (1996).
Laurent, et al., *Abstract No. 299,* for "Injectable Gel–Giving Solutions for Embolization. Hydrodynamic and Animal Studies" Meeting of Interventional Radiology (1996).
Chaloupka, *Amer. Jour. Neur. Rad.,* "Technical Feasibility and Histopathologic Studies of Ethylene Vinyl Copolymer (EVAL) Using a Swine Endovascular Embolization Model" 15:1107–115 (1994).

*Primary Examiner*—Manuel Mendez
*Attorney, Agent, or Firm*—Burns, Doane, Swecker & Mathis, L.L.P.

[57] ABSTRACT

Disclosed are novel methods for embolizing blood vessels which are particularly suited for treating vascular lesions via catheter delivery of an embolic composition comprising a biocompatible polymer and an embolic solvent.

17 Claims, 1 Drawing Sheet

METHODS FOR EMBOLIZING VASCULAR SITES WITH AN EMBOILIZING COMPOSITION COMPRISING DIMETHYLSULFOXIDE

BACKGROUND OF THE INVENTION

1. Field of the Invention

This invention is directed to novel methods for the catheter delivery to a vascular site of embolizing compositions which are particularly suited for treating vascular lesions. In particular, the methods of this invention comprise the vascular delivery of an embolizing composition comprising a biocompatible, water insoluble polymer and an embolic solvent such as dimethylsulfoxide.

The methods of this invention overcome art recognized problems including vasospasms associated with vascular delivery of compositions comprising an embolic solvent such as dimethylsulfoxide.

References

The following publications are cited in this application as superscript numbers:

[1] Mandai, et al., "Direct Thrombosis of Aneurysms with Cellulose Acetate Polymer", J. Neurosurg., 77:497–500 (1992)

[2] Kinugasa, et al., "Direct Thrombosis of Aneurysms with Cellulose Acetate Polymer", J. Neurosurg., 77:501–507 (1992)

[3] Casarett and Doull's Toxicology, Amdur et al., Editors, Pergamon Press, New York, pp. 661–664 (1975)

[4] Greff, et al., U.S. patent application Ser. No. 08/507,863 for "Novel Compositions for Use in Embolizing Blood Vessels", filed Jul. 27, 1995

[5] Greff, et al., U.S. patent application Ser. No. 08/508,248 for "Cellulose Diacetate Compositions for Use in Embolizing Blood Vessels", filed Jul. 27, 1995

[6] Kinugasa, et al., "Early Treatment of Subarachnoid Hemorrhage After Preventing Rerupture of an Aneurysm", J. Neurosurg., 83:34–41 (1995)

[7] Kinugasa, et al., "Prophylactic Thrombosis to Prevent New Bleeding and to Delay Aneurysm Surgery", Neurosurg., 36:661 (1995)

[8] Taki, et al., "Selection and Combination of Various Endovascular Techniques in the Treatment of Giant Aneurysms", J. Neurosurg., 77:37–42 (1992)

[9] Evans, et al., U.S. patent application Ser. No. 08/655,822 for "Novel Compositions for Use in Embolizing Blood Vessels", filed May 31, 1996.

[10] Sampei, et al., Interventional Neuroradiology, for "Histological Changes in Brain Tissue and Vasculature after Intracarotid Infusion of Organic Solvents in Rats", 38:291 (1996)

[11] Laurent, et al., Abstract No. 299, for "Injectable Gel-Giving Solutions for Embolization. Hydrodynamic and Animal Studies" Meeting of Interventional Radialogy (1996).

[12] Chaloupka, Amer. Jour. Neur. Rad., 15:1107 (1994)

All of the above references are herein incorporated by reference in their entirety to the same extent as if each individual reference was specifically and individually indicated to be incorporated herein by reference in its entirety.

2. State of the Art

Embolization of blood vessels is conducted for a variety of purposes including the treatment of tumors, the treatment of lesions such as aneurysms, arteriovenous malformations (AVM), arteriovenous fistula (AVF), uncontrolled bleeding and the like.

Embolization of blood vessels is preferably accomplished via catheter techniques which permit the selective placement of the catheter at the vascular site to be embolized. In this regard, recent advancements in catheter technology as well as in angiography now permit neuro endovascular intervention including the treatment of otherwise inoperable lesions. Specifically, development of microcatheters and guide wires capable of providing access to vessels as small as 1 mm in diameter allows for the endovascular treatment of many lesions.

Catheter embolization employs embolic compositions which preferably comprise an embolic solvent such as ethanol, dimethylsulfoxide (DMSO) or aqueous solutions of ethanol or DMSO and a biocompatible, water insoluble polymer. In a particularly preferred embodiment, the embolic composition further comprises a contrast agent and, in particular a water insoluble contrast agent. The contrast agent is employed in order that the physician can visualize delivery of the embolic composition to the vascular site via conventional techniques such as fluoroscopy.[1-8]

In embolic procedures, the embolic solvent is selected to be miscible or soluble in blood or other body fluid and to solubilize the water insoluble biocompatible polymer during delivery. The biocompatible polymer is selected to be soluble in the embolic solvent but insoluble in blood or other body fluid. The contrast agent is suspended in the composition and, as above, is selected to permit the physician to fluoroscopically visualize catheter delivery of this composition. Upon contact with the blood or other body fluid, the embolic solvent dissipates from the embolic composition whereupon the biocompatible polymer precipitates in the presence of the water insoluble contrast agent and embolizes the blood vessel.

In practice, complications in this procedure have, however, been reported when using known embolization methods via catheter delivery of the embolizing composition to the vascular site. For example, Sampei, et al.[10], Laurent, et al.[11] and Chaloupka[12] report that intra-arterial infusion of embolizing compositions containing even a small volume of DMSO produces local toxicity on the blood vessel.

Specifically, Chaloupka reported vasospasms, hemorrhage and ultimately death in the laboratory animals injected with DMSO and concluded that DMSO was angiotoxic. Sampei, et al.[10] report severe vasospasms arising from intra-arterial infusion of DMSO, which often results in cerebral infarction, and at a larger volume gross, angionecrosis of small cerebral arteries resulting in subarachnoid hemorrhage. Sampei, et al.[10] further report that the intra-arterial infusion of anhydrous DMSO or concentrated ethanol (e.g., 70% ethanol) can produce severe histopathological changes and can possible accelerate thrombosis of vessels distal to the injection. Based on the above, Sampei, et al.[10] conclude that the embolic composition should contain a low concentration of ethanol.

Notwithstanding the above, the use of an embolic solvent such as DMSO or concentrated ethanol in the embolizing composition is preferred for practical reasons including the fact that high concentrations of a water insoluble polymer composition are easier to generate in DMSO or concentrated ethanol than in dilute ethanol. In view of the above, there is an ongoing need to develop methods which permit the catheter delivery of an embolizing composition comprising DMSO or concentrated ethanol to the vascular sites.

SUMMARY OF THE INVENTION

This invention is directed to the novel and unexpected discovery that the method of catheter delivery of the embolizing composition comprising DMSO or concentrated ethanol is critical to embolizing the vascular site while inhibiting vasospasms and other adverse reactions. Specifically, this invention is based, in part, on the discovery that mammalian vasospasms arising from the intra-vascular delivery of the embolic solvent is concentration dependent at the in vivo injection site and that such vasospasms can be inhibited by controlling the injection rate of the embolic solvent such that its in vivo concentration does not exceed that required to initiate vasospasms.

Accordingly, in one of its method aspects, this invention is directed to a method for intra-vascular delivery to a mammal of an embolic composition while inhibiting vasospasms in the mammal which method comprises:

(a) selecting an embolic composition comprising a biocompatible, water insoluble polymer and an embolic solvent; and (b) intra-vascularly injecting the composition selected in (a) above into the mammal at a flow rate such that the concentration of the embolic solvent in a given blood volume is maintained at a level insufficient to initiate vasospasms.

In a particularly preferred aspect of this invention, the embolic composition further comprises a contrast agent and preferably a water insoluble contrast agent.

A further method aspect of this invention is directed to a specific method for ensuring controlled delivery of an embolic composition to a selected intra-vascular injection site of a mammal. In particular, this aspect is directed to a method for the catheter delivery of an embolic composition comprising a biocompatible polymer, a water insoluble biocompatible contrast agent, and an embolic solvent to an intra-vascular injection site of a mammal which method comprises:

(a) select a microcatheter comprising a luer hub and a delivery means;

(b) insert the delivery means of the microcatheter selected in (a) above into a to-be-embolized vascular site of a mammal and confirming placement in vivo with a water soluble contrast agent;

(c) connect a syringe to the microcatheter luer hub and flushing any remaining water soluble contrast agent from the microcathether hub and delivery means with a solution comprising water (e.g., saline);

(d) add at least 0.50 cc of the embolic solvent to a second syringe;

(e) attach the second syringe prepared in (d) above to the microcatheter luer hub and then inject no more than about 0.3 cc of the embolic solvent into vascular site to flush out the aqueous contrast agent;

(f) remove the second syringe from the luer hub and then overfill/wash the luer hub of the microcatheter with the balance of the embolic solvent;

(g) connect a syringe comprising an embolic composition to the microcatheter hub while ensuring that air does not enter into the hub during connection wherein the embolic composition comprises an embolic solvent, a biocompatible polymer dissolved in the solvent, and a water insoluble biocompatible contrast agent dispersed therein;

(h) create a sharp interfacial boundary between the embolic solvent and the embolic composition;

(i) inject over about a 1 minute period sufficient amount of the embolic composition to displace the DMSO in the microcatheter; and (j) inject the embolic composition into the vascular site.

Preferably, in the methods of this invention, the embolizing composition comprises from about 2.5 to about 8.0 weight percent of a biocompatible polymer; from about 10 to about 40 weight percent of a water insoluble, biocompatible contrast agent having an average particle size of about 10 μm or less; and from about 52 to about 87.5 weight percent of an embolic solvent selected from dimethylsulfoxide or ethanol wherein the weight percent of the polymer, contrast agent and embolic solvent is based on the total weight of the complete composition.

In a further preferred embodiment, the water insoluble, biocompatible contrast agent is selected from the group consisting of barium sulfate, tantalum powder and tantalum oxide.

In still a further preferred embodiment, the embolic solvent is dimethylsulfoxide (DMSO).

In a particularly preferred embodiment, the injection rate of the embolic solvent is maintained at a rate of no more than about 0.8 vol. % DMSO/cc of blood/minute and preferably no more than 0.6 vol. % DMSO/cc of blood/minute. At this rate, the in vivo concentration of DMSO does not exceed that required to initiate vasospasms.

In one of its kit aspects, this invention is directed to a kit of parts comprising:

(a) a vial comprising a polymer composition comprising a biocompatible polymer, a contrast agent and an embolic solvent; and (b) a vial comprising an embolic solvent free of any biocompatible polymer and contrast agent.

In another of its kit aspects, this invention is directed to a kit of parts comprising:

(a) a vial comprising a polymer composition comprising a biocompatible polymer, a biocompatible water insoluble contrast agent, and dimethylsulfoxide;

(b) a vial comprising dimethylsulfoxide free of a biocompatible polymer and water insoluble contrast agent; and (c) a catheter.

In still a further preferred embodiment, the kit further comprises a microballoon catheter to attenuate blood flow.

In another preferred embodiment, the kit employs a syringe with a tapered injection port to minimize dead space.

DETAILED DESCRIPTION OF THE INVENTION

Figure 1:
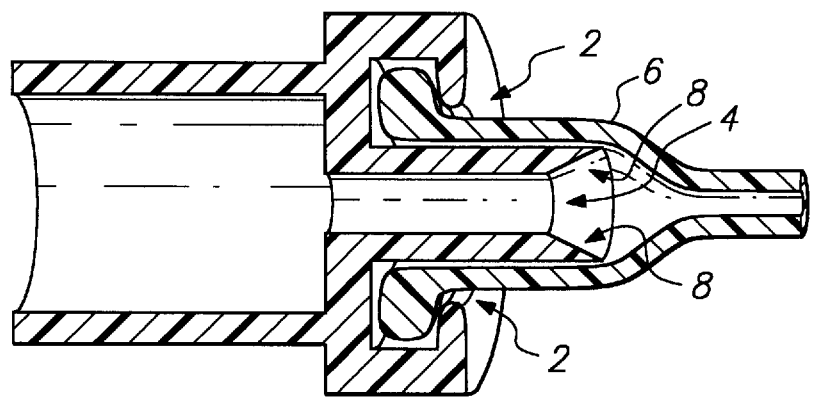
FIG. 1 illustrates a vertical cross-sectional view of a preferred microcatheter luer head and preferred syringe for use in the claimed invention.

This invention is directed to novel methods for embolizing blood vessels with an embolic composition which are particularly suited for treating vascular lesions via catheter delivery of the composition while inhibiting vasospasms arising from the intra-vascular injection of the embolic solvent.

However, prior to discussing this invention in further detail, the following terms will first be defined:

The term "embolizing" refers to a process wherein a material is injected into a blood vessel which, in the case of, for example, aneurysms, fills or plugs the aneurysm sac and/or encourages clot formation so that blood flow into the aneurysm ceases, and in the case of AVM's and AVF's forms a plug or clot to control/reroute blood flow to permit proper tissue perfusion. Embolization of the blood vessel is, therefore, important in preventing/controlling bleeding due to lesions (e.g., organ bleeding, gastrointestinal bleeding, vascular bleeding as well as bleeding associated with an aneurysm). In addition, embolization can be used to ablate diseased tissue (e.g., tumors, etc.) by cutting off its blood supply.

The term "biocompatible polymer" refers to polymers which, in the amounts employed, are non-toxic, chemically inert, and substantially non-immunogenic when used internally in the patient and which are substantially insoluble in blood and other aqueous solutions but are soluble in the embolic composition to the degree necessary to embolize a vascular site. Suitable biocompatible polymers include, by way of example, cellulose acetates[2,6–7] (including cellulose diacetate[5]), ethylene vinyl alcohol copolymers[4,8], hydrogels (e.g., acrylics), polyacrylonitrile, polyvinylacetate, cellulose acetate butyrate, nitrocellulose, copolymers of urethane/carbonate, copolymers of styrene/maleic acid, and mixtures thereof[9]. Preferably, the biocompatible polymer is also non-inflammatory when employed in situ.

The particular biocompatible polymer employed is not critical and is selected relative to the viscosity of the resulting polymer solution, the solubility of the biocompatible polymer in the embolic solvent, and the like. Such factors are well within the skill of the art.

Preferred biocompatible polymers include cellulose diacetate and ethylene vinyl alcohol copolymer. Cellulose diacetate polymers are either commercially available or can be prepared by art recognized procedures. In a preferred embodiment, the number average molecular weight, as determined by gel permeation chromatography, of the cellulose diacetate composition is from about 25,000 to about 100,000 more preferably from about 50,000 to about 75,000 and still more preferably from about 58,000 to 64,000. The weight average molecular weight of the cellulose diacetate composition, as determined by gel permeation chromatography, is preferably from about 50,000 to 200,000 and more preferably from about 100,000 to about 180,000. As is apparent to one skilled in the art, with all other factors being equal, cellulose diacetate polymers having a lower molecular weight will impart a lower viscosity to the composition as compared to higher molecular weight polymers. Accordingly, adjustment of the viscosity of the composition can be readily achieved by mere adjustment of the molecular weight of the polymer composition.

Ethylene vinyl alcohol copolymers comprise residues of both ethylene and vinyl alcohol monomers. Small amounts (e.g., less than 5 mole percent) of additional monomers can be included in the polymer structure or grafted thereon provided such additional monomers do not alter the embolizing properties of the composition. Such additional monomers include, by way of example only, maleic anhydride, styrene, propylene, acrylic acid, vinyl acetate and the like.

Ethylene vinyl alcohol copolymers are either commercially available or can be prepared by art recognized procedures. Preferably, the ethylene vinyl alcohol copolymer composition is selected such that a solution of 6 weight percent of the ethylene vinyl alcohol copolymer, 35 weight percent of a tantalum contrast agent in DMSO has a viscosity equal to or less than 60 centipoise at 20° C. As is apparent to one skilled in the art, with all other factors being equal, copolymers having a lower molecular weight will impart a lower viscosity to the composition as compared to higher molecular weight copolymers. Accordingly, adjustment of the viscosity of the composition as necessary for catheter delivery can be readily achieved by mere adjustment of the molecular weight of the copolymer composition.

As is also apparent, the ratio of ethylene to vinyl alcohol in the copolymer affects the overall hydrophobicity/hydrophilicity of the composition which, in turn, affects the relative water solubility/insolubility of the composition as well as the rate of precipitation of the copolymer in an aqueous solution (e.g., blood). In a particularly preferred embodiment, the copolymers employed herein comprise a mole percent of ethylene of from about 25 to about 60 and a mole percent of vinyl alcohol of from about 40 to about 75. These compositions provide for requisite precipitation rates suitable for use in embolizing blood vessels.

The term "contrast agent" refers to both water insoluble and water soluble contrast agents.

"Water insoluble contrast agents" refer to a water insoluble (i.e., has a water solubility of less than 0.01 mg/ml at 20° C.), radiopaque material capable of being monitored during injection into a mammalian subject by, for example, radiography. Examples of water insoluble contrast agents include tantalum, tantalum oxide and barium sulfate, which are commercially available in the proper form for in vivo use. Preferably, the water insoluble contrast agent has an average particle size of about 10 μm or less. Methods for preparing such water insoluble biocompatible contrast agents having an average particle size of about 10 μm or less are described below. Other water insoluble contrast agents include gold, tungsten and platinum.

The term "water soluble contrast agent" refers to a water soluble, biocompatible (non-toxic) radiopaque material capable of being monitored during injection into a mammalian subject by, for example, radiography.

Examples of water soluble contrast agents include metrizamide, iopamidol, iothalamate sodium, iodomide sodium, and meglumine.

The term "embolic solvent" refers to solvents capable of dissolving the selected biocompatible polymer, are miscible or soluble in aqueous compositions (e.g., blood) and which cause intra-vascular spasms when delivered to the vascular site via prior art techniques. Suitable embolic solvents include ethanol, dimethylsulfoxide, acetone, and the like as well as aqueous mixtures thereof having no more than about 30 percent water. When employed at this level, the amount of water is sufficiently small that the dissolved polymer precipitates upon contact with the blood. Preferably, the embolic solvent is anhydrous and, even more preferably, the embolic solvent is anhydrous dimethylsulfoxide.

The term "encapsulation" as used relative to the contrast agent being encapsulated in the polymer precipitate is not meant to infer any physical entrapment of the contrast agent within the precipitate much as a capsule encapsulates a medicament. Rather, this term is used to mean that an integral coherent precipitate forms which does not separate into individual components.

Compositions

The polymer or compositions employed in the methods of this invention are prepared by conventional methods whereby each of the components is added and the resulting composition mixed together until the overall composition is substantially homogeneous.

For example, polymer compositions can be prepared by adding sufficient amounts of the biocompatible polymer to the embolic solvent to achieve the effective concentration for the polymer composition. Preferably, the polymer composition will comprise from about 2.5 to about 8.0 weight percent of the biocompatible polymer composition based on the total weight of the polymer composition and more preferably from about 4 to about 5.2 weight percent. If necessary, gentle heating and stirring can be used to effect dissolution of the biocompatible polymer into the embolic solvent, e.g., 12 hours at 50° C.

Sufficient amounts of the contrast agent are then added to the embolic solvent to achieve the effective concentration for the complete composition. Preferably, the composition will comprise from about 10 to about 40 weight percent of a contrast agent and more preferably from about 20 to about 40 weight percent and even more preferably about 30 weight percent. When the contrast agent is not soluble in the embolic solvent, stirring is employed to effect homogeneity of the resulting suspension. In order to enhance formation of the suspension, the particle size of the contrast agent is preferably maintained at about 10 μm or less and more preferably at from about 1 to about 5 μm (e.g., an average size of about 2 μm). In one preferred embodiment, the appropriate particle size of the contrast agent is prepared, for example, by fractionation. In such an embodiment, a water insoluble contrast agent such as tantalum having an average particle size of less than about 20 microns is added to an organic liquid such as ethanol (absolute) preferably in a clean environment. Agitation of the resulting suspension followed by settling for approximately 40 seconds permits the larger particles to settle faster. Removal of the upper portion of the organic liquid followed by separation of the liquid from the particles results in a reduction of the particle size which is confirmed under an optical microscope. The process is optionally repeated until a desired average particle size is reached. See, for example, Greff, et al. U.S. patent application Ser. No. 08/688,050, filed Jul. 29, 1996 which is incorporated herein by reference in its entirety.

The particular order of addition of components to the embolic solvent is not critical and stirring of the resulting suspension is conducted as necessary to achieve homogeneity of the composition. Preferably, mixing/stirring of the composition is conducted under an anhydrous atmosphere at ambient pressure. The resulting composition is heat sterilized and then stored preferably in sealed clear or amber bottles or vials until needed.

The polymers recited herein are typically commercially available but can also be prepared by methods well known in the art. For example, polymers are typically prepared by conventional techniques such as radical, thermal, UV, γ irradiation, or electron beam induced polymerization employing, as necessary, a polymerization catalyst or polymerization initiator to provide for the polymer composition. The specific manner of polymerization is not critical and the polymerization techniques employed do not form a part of this invention.

In order to maintain solubility in the embolic solvent, the polymers described herein are preferably not cross-linked.

Methods

The compositions described above can then be employed in methods for the catheter assisted intra-vascular embolization of mammalian blood vessels. The methods of this invention are employed at intra-vascular sites wherein blood flow is attenuated but not arrested. Attenuation of blood flow arises by placement of the catheter into the vascular site which results in reduced flow through. Additionally, a microballoon can be employed to further attenuate blood flow.

In the methods of this invention, a sufficient amount of this composition is introduced into the selected blood vessel via a catheter delivery means under fluoroscopy so that upon precipitation of the polymer the blood vessel is embolized. The particular amount of embolizing composition employed is dictated by the total volume of the vasculature to be embolized, the concentration of polymer in the composition, the rate of precipitation (solids formation) of the polymer, etc. Such factors are well within the skill of the art.

In the catheter delivery methods described herein, a small diameter medical catheter (i.e., microcatheter) having a diameter typically from about 1 to about 3 mm is employed. The particular catheter employed is not critical provided that polymeric catheter components are compatible with the embolizing composition (i.e., the catheter components will not readily degrade in the embolizing composition). In this regard, it is preferred to use polyethylene in the catheter components because of its inertness in the presence of the embolizing composition described herein. Other materials compatible with the embolizing compositions can be readily determined by the skilled artisan and include, for example, other polyolefins, fluoropolymers (e.g., polytetrafluoroethylene, perfluoroalkoxy resin, fluorinated ethylene propylene polymers, etc.), silicone, etc. The specific polymer employed is selected relative to stability in the presence of DMSO and preferably has lubricious properties.

Central to one aspect of the claimed invention is the specific catheter delivery technique for delivering the embolic composition comprising the herein described embolic solvent while inhibiting vasospasms. Specifically, this technique encompasses the following:

1. Shake the embolic composition comprising the biocompatible polymer, the embolic solvent and the biocompatible water insoluble contrast agent for about 4 minutes until the contrast agent is fully dispersed;
2. Place the delivery means of the microcatheter at the site of intended vascular embolization while confirming microcatheter placement in vivo by injection of water soluble contrast agent;
3. Connect a syringe containing saline to the luer hub of the microcatheter and flush the water soluble contrast agent from the microcatheter hub and body with about 5 cc of saline over an approximately 1 minute period with gentle pulsing at 1 cc increments. Repeat with another 5 cc of saline if the volume can be tolerated. Leave the syringe connected or secure a cap on the microcatheter luer hub;
4. Aspirate 0.5 cc of sterile DMSO into a 1 cc syringe. Remove cap from microcatheter hub. Inject 0.20 cc of DMSO for a typical 75 cm microcatheter or 0.30 cc of DMSO for a typical 150 cm microcatheter. While the DMSO is being prepared and injected, shake the embolic composition for about 2 minutes to fully disperse the water insoluble contrast agent. Fill a 1 cc syringe with the embolic composition using a 21 gage needle. As soon as the DMSO has been injected, remove the syringe and overfill/wash the balance of the DMSO;
5. Immediately connect the syringe containing the embolic composition to the catheter hub, making sure that there is no air in the hub during the connection;
6. With the composition syringe pointing up to create a sharp interfacial boundary between the DMSO and the embolic composition, slowly inject the first 0.15 cc (75 cm catheter) or 0.25 cc (150 cm catheter) over a 1 minute period to displace the DMSO in the microcatheter and dilute the DMSO in the blood;

7. Under fluoroscopy, the embolic composition may be visible in the distal portion of the microcatheter body. Lower the syringe tip and inject the embolic composition as the clinical situation requires. Monitor the volume of the embolic composition injected to correspond to the volume of the vascular space being filled; and 8. Upon completion of the embolic composition injection, gently aspirate with the embolic syringe to separate the catheter tip from the embolic composition mass. Wait a few seconds, release the syringe plunger and withdraw the microcatheter.

In this protocol, the dead space for the 150 cm microcatheter is about 0.32 cc.

In the case of aneurysms, the mammal is preferably rotated to place the aneurysm in a downward position to encourage displacement of aneurysmal blood upon injection.

When introduced into the vascular site, the embolic solvent diffuses rapidly into the blood and a solid precipitate forms which precipitate is the water insoluble polymer with the contrast agent encapsulated therein. Without being limited to any theory, it is believed that initially, a soft gel to spongy solid precipitate forms upon contact with the blood. This precipitate then restricts blood flow, entrapping red cells thereby causing clot embolization of the blood vessel.

A particularly preferred microcatheter/syringe combination for use in this delivery method is set forth in FIG. 1 which illustrates the interface between the syringe and the microcatheter at the luer hub. Specifically, in FIG. 1, the luer hub/syringe interface 2 is formed by mating the terminal injection site 4 of the syringe with the luer hub 6 which secures the syringe to the microcatheter. The walls 8 of the injection port of the syringe are preferably tapered to prevent settling of insoluble material behind these walls.

Figure 2:
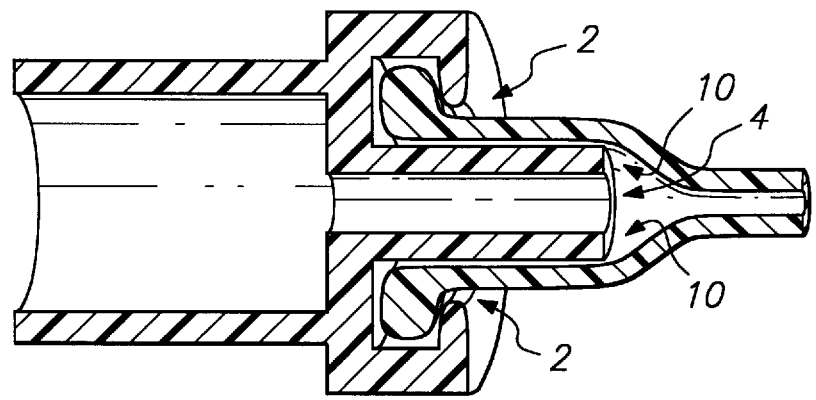
FIG. 2 illustrates in vertical cross-section the dead spaces formed by a conventional injection port for a syringe when fitted in combination with the microcatheter.

FIG. 2 illustrates that this tapering feature is particularly important since non-tapered walls of a convential injection port will allow the formation of dead spaces 10 behind these walls as the fluid compositions flow past. Such dead spaces invariably result in vortexes forming which concomittantly results in retention of materials flowing there past such as the aqueous solution of the water soluble contrast agent. Upon injection of the embolic composition, contact of this composition with the vortexed aqueous solution results in the precipitation of the biocompatible polymer which can result in plugging of the microcatheter orifice.

Figure 3:
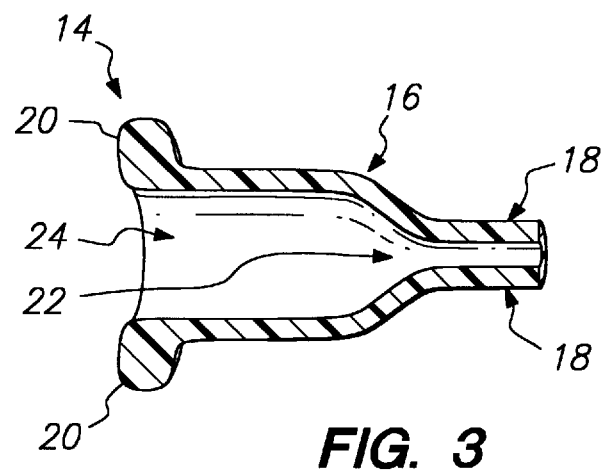
FIG. 3 illustrates a vertical cross-sectional view of the luer hub of FIG. 1 without the attached syringe.

FIG. 3 illustrates the catheter luer hub of FIG. 1 without the attached syringe. In this embodiment, the protrusions 20 of luer hub 16 mate with the syringe (not shown) to secure the syringe to the catheter 14. The walls 18 of the luer hub 16 taper quickly to orifice 22 which defines the internal passage in the delivery means of catheter 14. Rapid tapering reduces the dead space 24 of the luer hub 16 and results in a tight fit with the syringe when so fitted. Preferably, the dead space is less than about 0.2 cc and more preferably less than about 0.1 cc. When so limited, mixing of different solutions in the dead space of the luer hub is minimized. Such mixing can occur, for example, during steps 4 and/or 6 (described above). In either case, mixing is detrimental to the overall efficient delivery of the embolic composition. For example, any water retained in the luer hub after step 3 can result in precipitation of the biocompatible polymer upon introduction of the embolic composition into the catheter thereby possibly clogging the catheter. Similarly, any embolic solvent retained in the luer hub after step 4 can result in dilution of the embolic composition in step 7 which renders fluoroscopic detection of the initial mass injected more difficult.

It is contemplated that the luer hub could be modified to include multiple injection ports which would permit the attachment of multiple syringes simultaneously to the luer hub which, in turn, would permit the serial injection of the different solutions employed in this protocol.

In the methods of this invention, it is necessary to ensure that the in vivo concentration of the embolic solvent does not exceed that required to initiate vasospasms at the intravasculare injection site. This can be achieved by carefully controlling the injection rate of the embolic composition to maintain a very low concentration of the embolic solvent.

The intra-vascular site, however, is a dynamic, in-flux fluid system wherein the concentration of the embolic solvent decreases rapidly from the injection site to a point downstream therefrom. Accordingly, for the purposes of this invention, the concentration of the embolic solvent is measured at a point about 3 centimeters downstream of the injection site. When so measured, it has been found that injection rates of the embolic solvent of about 0.5 volume percent/cc blood/minute or less are sufficiently low to inhibit vasospasms at the intra-vascular site.

Utility

The methods described herein are useful in embolizing mammalian blood vessels which, in turn, can be used to prevent/control bleeding (e.g., organ bleeding, gastrointestinal bleeding, vascular bleeding, bleeding associated with an aneurysm) or to ablate diseased tissue (e.g., tumors, etc.). Accordingly, these methods find use in human and other mammalian subjects requiring embolization of blood vessels.

The following examples are set forth to illustrate the claimed invention and are not to be construed as a limitation thereof.

EXAMPLES

Unless otherwise stated, all temperatures are in degrees Celsius. Also, in these examples and elsewhere, the following abbreviations have the following meanings:

cc=cubic centimeter cm=centimeter

DMSO 32 dimethylsulfoxide

EVOH=ethylene vinyl alcohol copolymer g=gram

ID=internal diameter in.=inch min.=minute mL=milliliter mm=millimeter

OD=outer diameter sec.=seconds

μm=micron

Example 1

The purpose of this example is to demonstrate the preparation of a polymer composition useful in the methods of this invention.

Specifically, an EVOH polymer composition was prepared as follows:

Composition

A) 8 gm EVOH;

B) 30 gm tantalum having an average particle size of about 3 μm (narrow size distribution); and C) 100 mL DMSO.

Each of the components of this composition were combined and the resulting mixture was mixed until homogeneous.

In this composition, the average particle size of the contrast agent was prepared by fractionation wherein tantalum, having an average particle size of less than about 20 μm, was added to ethanol (absolute) in a clean environment. Agitation of the resulting suspension was followed by settling for approximately 40 sec. to permit the larger particles to settle faster. Removal of the upper portion of the ethanol followed by separation of the liquid from the particles results in a reduction of the particle size which is confirmed under a microscope (Nikon Alphaphot™). The process was repeated, as necessary, until an average 3 μm particle size was reached.

Example 2

The purpose of this example is to illustrate a specific protocol for embolizing mammalian blood vessels via the methods of this invention. This example employed a 20 kg red Duroc swine with rete mirabile located in the lower portions (left and right) of the skull base.

The swine was anesthetized. The embolic composition of Example 1 above was shaken for about 4 minutes until the contrast agent was fully dispersed. A 150 cm microcatheter was placed through a femoral artery access at the site of intended vascular embolization, the rete mirabile (a well accepted AVM model) using a 0.014 inch guidewire while confirming microcatheter placement by injection of water soluble contrast agent (e.g., Omnipaque™ available from Nycomed, Princeton, N.J.). After placement, a syringe containing saline was connected to the luer hub of the microcatheter and the water soluble contrast agent was flushed from the microcatheter hub and body with about 5 cc of saline over an approximately 1 minute period with gentle pulsing at 1 cc increments. Afterwards, the syringe was removed and a cap was secured on the microcatheter luer hub.

Sterile DMSO (0.5 cc) was aspirated into a 1 cc syringe. The cap was removed from the microcatheter hub and the syringe fitted thereto. About 0.30 cc of DMSO was injected into the catheter to remove the saline therefrom.

While the DMSO was being prepared and injected, the embolic composition was shaken for about 2 minutes to fully disperse the water insoluble contrast agent. A 1 cc syringe was then filled with the embolic composition using a 21 gage needle. As soon as the DMSO has been injected, the syringe was removed and the balance of the DMSO used for overfilling and washing the luer hub.

Afterwards, the syringe containing the embolic composition was immediately connected to the catheter hub, making sure that there was no air in the hub during the connection. With the composition syringe pointing up to create a sharp interfacial boundary between the DMSO and the embolic composition, the first 0.25 cc was injected over a 1 minute period to displace the DMSO in the microcatheter and dilute the DMSO in the blood. Under fluoroscopy, the embolic composition was visible in the distal portion of the microcatheter body. The syringe tip was lowered and the embolic composition then injected as the clinical situation requires. The volume of the embolic composition was monitored to ensure that the amount of embolic composition injected corresponded to the volume of the vascular space being filled (about 0.2 cc). Upon completion of the embolic composition injection, the embolic syringe was gently aspirated to separate the catheter tip from the embolic composition mass. After a few seconds, the syringe plunger was released and the microcatheter withdrawn.

From the foregoing description, various modifications and changes in the composition and method will occur to those skilled in the art. All such modifications coming within the scope of the appended claims are intended to be included therein.

What is claimed is:

1. A method for intra-vascular delivery to a mammal of an embolic composition while inhibiting vasospasms in the mammal which method comprises:
   (a) selecting an embolic composition comprising a biocompatible, water insoluble polymer and an embolic solvent; and
   (b) intra-vascularly injecting the composition selected in (a) above into the mammal at a flow rate such that the concentration of the embolic solvent in a given blood volume is maintained at a level insufficient to initiate vasospasms.

2. The method according to claim 1 wherein said embolic solvent is dimethylsulfoxide.

3. The method according to claim 1 wherein the embolic composition further comprises a contrast agent.

4. The method according to claim 3 wherein the contrast agent is a water insoluble contrast agent.

5. The method according to claim 4 wherein said water insoluble contrast agent is selected from the group consisting of tantalum, tantalum oxide, tungsten and barium sulfate.

6. The method according to claim 4 wherein said water insoluble contrast agent is tantalum.

7. The method according to claim 1 wherein said biocompatible polymer is selected from the group consisting of cellulose acetates, ethylene vinyl alcohol copolymers, hydrogels, polyacrylonitrile, polyvinylacetate, cellulose acetate butyrate, nitrocellulose, copolymers of urethane/carbonate, copolymers of styrene/maleic acid, and mixtures thereof.

8. The method according to claim 6 wherein said biocompatible polymer is an ethylene and vinyl alcohol copolymer.

9. The method according to claim 4 wherein said water insoluble contrast agent has an average particle size of about 10 microns or less.

10. A method for the catheter delivery of an embolic composition comprising a biocompatible polymer, a water insoluble biocompatible contrast agent, and an embolic solvent to an intra-vascular injection site of a mammal which method comprises:
   (a) select a microcatheter comprising a luer hub and a delivery means;
   (b) insert the delivery means of the microcatheter selected in (a) above into a to-be-embolized vascular site of a mammal and confirming placement in vivo with a water soluble contrast agent;
   (c) connect a syringe to the microcatheter luer hub and flushing any remaining water soluble contrast agent from the microcathether hub and delivery means with a solution comprising water;
   (d) add at least 0.50 cc of the embolic solvent to a second syringe;
   (e) attach the second syringe prepared in (d) above to the microcatheter luer hub and then inject no more than about 0.3 cc of the embolic solvent into vascular site to flush out the aqueous contrast agent;
   (f) remove the second syringe from the luer hub and then overfill/wash the luer hub of the microcatheter with the balance of the embolic solvent;

(g) connect a syringe comprising an embolic composition to the microcatheter hub while ensuring that air does not enter into the hub during connection wherein the embolic composition comprises an embolic solvent, a biocompatible polymer dissolved in the solvent, and a water insoluble biocompatible contrast agent dispersed therein;

(h) create a sharp interfacial boundary between the embolic solvent and the embolic composition;

(i) inject over about a 1 minute period sufficient amount of the solution to displace the DMSO in the microcatheter; and (j) inject the embolic composition into the vascular site at a flow rate such that the concentration of the embolic solvent in a given blood volume is maintained at a level which inhibits vasospasms.

11. The method according to claim 10 wherein said embolic solvent is dimethylsulfoxide.

12. The method according to claim 10 wherein said water insoluble contrast agent is selected from the group consisting of tantalum, tantalum oxide, tungsten and barium sulfate.

13. The method according to claim 12 wherein said water insoluble contrast agent is tantalum.

14. The method according to claim 10 wherein said biocompatible polymer is selected from the group consisting of cellulose acetates, ethylene vinyl alcohol copolymers, hydrogels, polyacrylonitrile, polyvinylacetate, cellulose acetate butyrate, nitrocellulose, copolymers of urethane/carbonate, copolymers of styrene/maleic acid, and mixtures thereof.

15. The method according to claim 14 wherein said biocompatible polymer is an ethylene and vinyl alcohol copolymer.

16. The method according to claim 10 wherein said water insoluble contrast agent has an average particle size of about 10 microns or less.

17. The method according to claim 10 wherein the luer hub comprises multiple injection ports thereby permitting the attachment of multiple syringes simultaneously to the luer hub.

\* \* \* \* \*